US012661275B2

(12) United States Patent
Aytuerk et al.

(10) Patent No.: US 12,661,275 B2
(45) Date of Patent: Jun. 23, 2026

(54) ABSORBENT ARTICLE

(71) Applicant: The Procter & Gamble Company, Cincinnati, OH (US)

(72) Inventors: Fatma Oya Aytuerk, Hessen (DE); Naka Seidel, Frankfurt (DE); Arnaldo Rafael Millan Malpica, Hessen (DE)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 301 days.

(21) Appl. No.: 18/450,088

(22) Filed: Aug. 15, 2023

(65) Prior Publication Data

US 2024/0050286 A1 Feb. 15, 2024

Related U.S. Application Data

(63) Continuation of application No. PCT/US2023/071886, filed on Aug. 9, 2023.

(60) Provisional application No. 63/396,428, filed on Aug. 9, 2022.

(51) Int. Cl.
| | |
|---|---|
| *A61F 13/472* | (2006.01) |
| *A61F 13/47* | (2006.01) |
| *A61F 13/511* | (2006.01) |
| *A61F 13/56* | (2006.01) |

(52) U.S. Cl.
CPC ........ *A61F 13/472* (2013.01); *A61F 13/4704* (2013.01); *A61F 13/51113* (2013.01); *A61F 13/5611* (2013.01); *A61F 2013/51117* (2013.01)

(58) Field of Classification Search
CPC .. A61F 13/4702; A61F 13/472; A61F 13/476; A61F 13/51113; A61F 13/5514; A61F 2013/51059; A61F 2013/51064; A61F 2013/51117
See application file for complete search history.

(56) References Cited

U.S. PATENT DOCUMENTS

| | | | | |
|---|---|---|---|---|
| 6,497,692 | B1 * | 12/2002 | Tameishi | A61F 13/5514 604/397 |
| 6,656,168 | B2 * | 12/2003 | Braverman | A61F 13/4755 424/443 |
| 7,388,123 | B2 * | 6/2008 | Cowell | A61F 13/51113 604/382 |
| 8,211,078 | B2 * | 7/2012 | Noel | A61F 13/15203 604/385.101 |
| 8,795,716 | B2 * | 8/2014 | Warren | A61F 13/51104 604/362 |
| 9,035,123 | B2 * | 5/2015 | Hammons | A61L 15/50 604/360 |
| 11,154,434 | B2 * | 10/2021 | Palmqvist | A61F 13/49 |
| 2003/0114812 | A1 | 6/2003 | Braverman et al. | |
| 2006/0206077 | A1 * | 9/2006 | Warren | A61F 13/84 604/385.05 |
| 2010/0191205 | A1 | 7/2010 | Carbonari et al. | |
| 2017/0135877 | A1 * | 5/2017 | Kudo | A61F 13/4756 |

OTHER PUBLICATIONS

PCT Search Report and Written Opinion for PCT/US2023/071886 dated Nov. 27, 2023, 11 Pages.

* cited by examiner

*Primary Examiner* — Catharine L Anderson
(74) *Attorney, Agent, or Firm* — Sarah M. DeCristofaro

(57) ABSTRACT

The invention relates to an absorbent article for external use. More specifically, the invention relates to a folded absorbent article having wings and a lotion pattern comprising lotion pattern area(s) disposed on the inner side edges of the wings.

11 Claims, 6 Drawing Sheets

ABSORBENT ARTICLE

FIELD OF THE INVENTION

The invention relates to an absorbent article for external use. More specifically, the invention relates to a folded absorbent article having wings and a lotion pattern comprising lotion pattern area(s) disposed on the inner side edges of the wings.

BACKGROUND OF THE INVENTION

Absorbent articles, such as sanitary napkins or pads, are used by women during their menstrual periods to receive and contain blood discharges from the vagina. In addition to collecting body fluids like menses, these articles are also expected to protect the wearer's undergarment from body fluid contamination. These articles typically comprise a liquid pervious topsheet as a body-facing layer, a backsheet as garment-facing layer, and an absorbent core between the topsheet and backsheet. The body fluids are acquired through the topsheet and subsequently stored in the absorbent core. The backsheet typically prevents the absorbed fluids from wetting the wearer's garment.

Absorbent articles typically comprise an adhesive on the garment-facing side of the backsheet, and the adhesive may be protected by a release film (e.g., a sheet of siliconized paper). Absorbent articles, such as sanitary napkins or pads, are commonly marketed in folded configurations, where the article is folded one, two, three, or more times around folding lines, which are usually parallel to the transverse centerline of the absorbent pad but can also be parallel to its longitudinal centerline and/or have any other direction. In the most common configuration, absorbent pads have two folding lines, which are parallel to the transverse axis of the absorbent pad. Typically, absorbent pads are folded and wrapped individually with a thin plastic (wrapper) film, the inner surface of which may be treated with a release agent, such as silicone; thus, the film itself can also act as release film protecting the adhesive and releasing it when the wrapper of the absorbent pad is removed.

Pads are designed to be worn in close proximity to the crotch of the wearer (e.g., placed between a wearer's crotch and her undergarment). Typically, pads are designed to be affixed to the wearer's undergarment so as to remain proximal the wearer's genitals and/or anus. Some pads comprise side flaps or wings, which are provided on the side edges of the pad and designed to fold around the crotch edges of an undergarment to protect the undergarment from side leakages. As the wearer moves about her daily life, however, the absorbent article may shift relative to the wearer's body may result in uncomfortable rubbing forces generated between the wearer and the absorbent article and concomitant skin irritation (e.g., at the inner thigh).

A known approach to address the effects of friction between the wearer and the absorbent article is to provide an absorbent article, such as a diaper, containing leg cuffs coated with lotion compositions, where the lotion compositions minimize abrasion between the cuffs and skin and reduce irritation in the area where the cuffs contact the wearer's skin. A folded absorbent pad having cuffs on each of its side edges that extend along the entire length of the article, where a skin care agent is provided on a skin surface side of the cuffs, is also known. Such known absorbent articles may reduce friction between the wearer's skin and the absorbent article, but these articles may have several disadvantages, for example, the lotion may have a negative impact on absorbency performance and/or create run-off leakage before transferring to a wearer's skin. In particular, in the context of a tri-folded absorbent pad, the application (or migration) of lotion outside of the central portion of the pad (the portion that lies between the two fold lines), especially onto the rear portion of the pad (which is generally folded over the central portion), may interfere with the packaging material/wrapper (resulting in smearing on the packaging material or leakage of the lotion) and/or the wings (particularly, the adhesive disposed on the garment-facing side of the wings).

There is therefore a need for an absorbent article having a lotion pattern that is optimized (e.g., dimensions and placement) to reduce friction between the absorbent article and the skin and provide skin care benefits, without adversely affecting the appearance or performance of the absorbent article.

SUMMARY OF THE INVENTION

The present disclosure relates to a folded absorbent pad having, in its flattened unfolded configuration, a longitudinal centerline and a transverse centerline, the pad comprising: a topsheet, a backsheet, an absorbent core disposed between the topsheet and the backsheet, wherein the topsheet and the backsheet are joined to form wings on the longitudinal sides of the pad; one or more folding lines that define a front portion, a central portion, and a rear portion of the pad; and a lotion pattern disposed on the body-facing surface of the topsheet, the lotion pattern comprising at least two lotion pattern areas disposed at the inner side edges of the wings, parallel to the longitudinal centerline, wherein the rear portion of the pad is substantially free of lotion pattern areas.

These and other features, aspects, and advantages of the present disclosure will become evident to those skilled in the art from a reading of the present disclosure.

DETAILED DESCRIPTION OF THE INVENTION

Figure 1A:
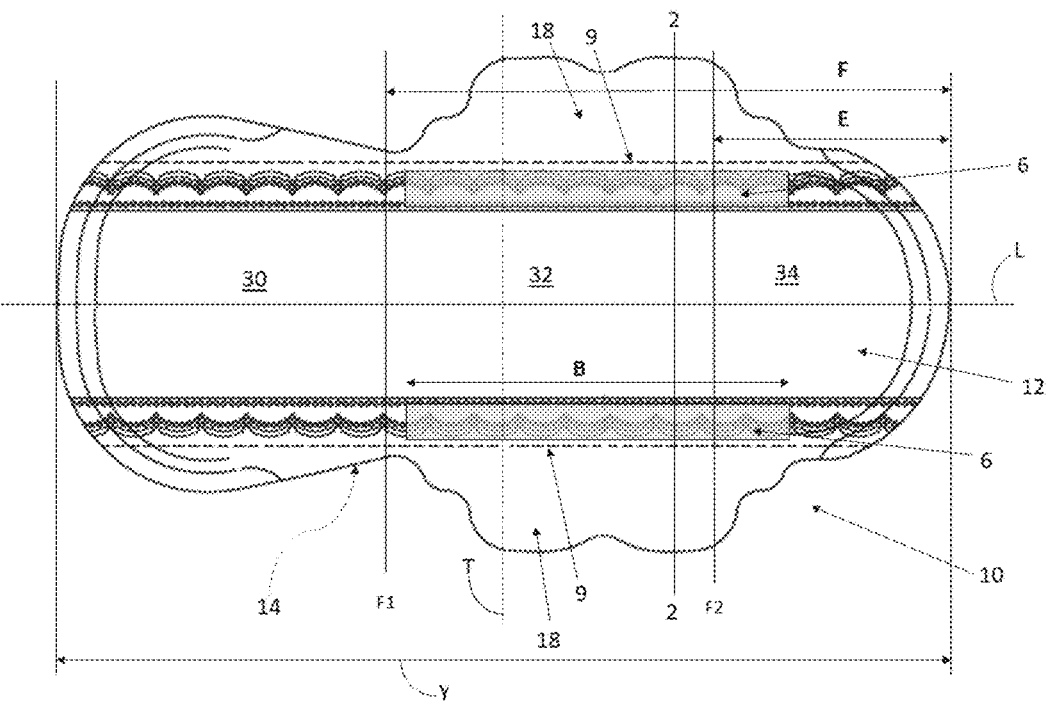
FIGS. 1a and 1b are top views of an exemplary absorbent article according to the present disclosure.

All ranges are inclusive and combinable. The number of significant digits conveys neither limitations on the indicated amounts nor on the accuracy of the measurements.

The term "absorbent article" is used herein in a broad sense including any article able to receive and/or absorb and/or contain and/or retain body fluids/bodily exudates, such as menses, vaginal secretions, and urine. Exemplary absorbent articles include disposable hygiene absorbent articles, such as feminine hygiene absorbent articles, e.g., sanitary napkins, panty liners, absorbent pads. Absorbent articles may include any types of structures, from single absorbent layers to more complex multi-layer structures.

As used herein, components are considered "absorbent" if such components not only transmit such liquids, but also can retain a portion of the liquids deposited on such components.

The term "disposable" is used herein to describe articles, which are not intended to be laundered or otherwise restored or reused as an article.

The term "longitudinal centerline", as used herein, refers to the line centered between the longitudinal side edges of the absorbent article and is generally aligned with the vertical plane which bisects a standing wearer into left and right body halves and is represented by the line L on the drawings. The length Y of the article indicates the longest length of the article in the longitudinal direction.

The term "transverse centerline", as used herein, refers to the imaginary line T centered between the transversal side edges of the absorbent article and which is perpendicular to the longitudinal centerline.

"Liquid impermeable"—refers to one or more properties or features of a film, web material or laminate thereof that cause(s) it to resist passage of aqueous liquid therethrough (from one major surface through to the other opposite major surface), under ordinary conditions of use of absorbent articles. A film, web material or laminate thereof may be liquid impermeable, but also vapor permeable ("breathable").

The term "liquid pervious" as used herein refers to components that allow liquids to pass therethrough without significantly retarding or obstructing the transmission of such liquids therethrough.

As used herein the term "flexible" refers to materials which are compliant and readily conform to the shape of the body or respond by easily deforming in the presence of external forces.

The term "hydrophilic", as used herein, describes fibers, surfaces of fibers, or surfaces of material which are wettable by aqueous fluids (e.g., aqueous body fluids) deposited on these fibers. Hydrophilicity and wettability may be defined in terms of contact angle and/or strike-through time of a fluid, e.g., through a material, as discussed in detail in the American Chemical Society Publication entitled "Contact Angle, Wettability and Adhesion", edited by Robert F. Could (Copyright 1964).

The term "nonwoven", as used herein, is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wetmilling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yam). Nonwoven fabrics can be formed by many processes such as meltblowing, spunbonding, solvent spinning, electro spinning, and carding. The basis weight of nonwoven fabrics is usually expressed in grams per square meter (gsm).

The term "joined" refers to the condition where a first component is affixed, or connected, to a second component either directly; or indirectly, where the first component is affixed, or connected, to an intermediate component which in turn is affixed, or connected, to the second component. The joined condition between the first component, and the second component, is intended to remain for the life of the sanitary napkin. Conversely, components are considered "removably affixed" if the components may be detached and separated from each other without destruction or unintended gross deformation of either.

With respect to an absorbent article, "body-facing" is a relative locational term referring to a feature of a component or structure of the article that, when in use, lies closer to the body of the wearer than another feature of the component or structure that lies along the same z-direction line. For example, a topsheet has a body-facing surface that lies closer to the wearer than the opposite, outward-facing surface of the topsheet.

With respect to an absorbent article, "outward-facing" is a relative locational term referring to a feature of a component or structure of the article that when in use that lies farther from the wearer than another feature of the component or structure that lies along the same z-direction line. For example, a topsheet has an outward-facing surface that lies farther from the wearer than the opposite, body-facing surface of the topsheet.

The terms "top," "bottom," "upper," "lower," "over," "under," "beneath," "superadjacent," "subjacent," and similar vertical positional terms, when used herein to refer to layers, components or other features of a wearable absorbent article, are to be interpreted with respect to the article as it would appear when opened and laid out flat on a horizontal surface, with its body-facing surface facing upward and outward-facing surface facing downward.

The term "inner side", as used herein, is defined as the direction toward the longitudinal centerline L of the absorbent article 10. The term "outer side" is defined as the opposite direction (away from the longitudinal centerline L and toward the longitudinal side edge(s) of the absorbent article).

The terms "bodily fluid(s)" or "fluid", as used herein, include, but are not limited to menses, vaginal discharges, blood, sweat, and combinations of these substances.

The term "ambient conditions" as used herein refers to surrounding conditions at about one atmosphere of pressure, at about 50% relative humidity, and at about 25° C.

Absorbent articles according to the present disclosure generally include a fluid pervious topsheet, a backsheet, which may be fluid impervious and/or may be water vapour and/or gas pervious, and an absorbent core comprised there between.

Figure 1B:
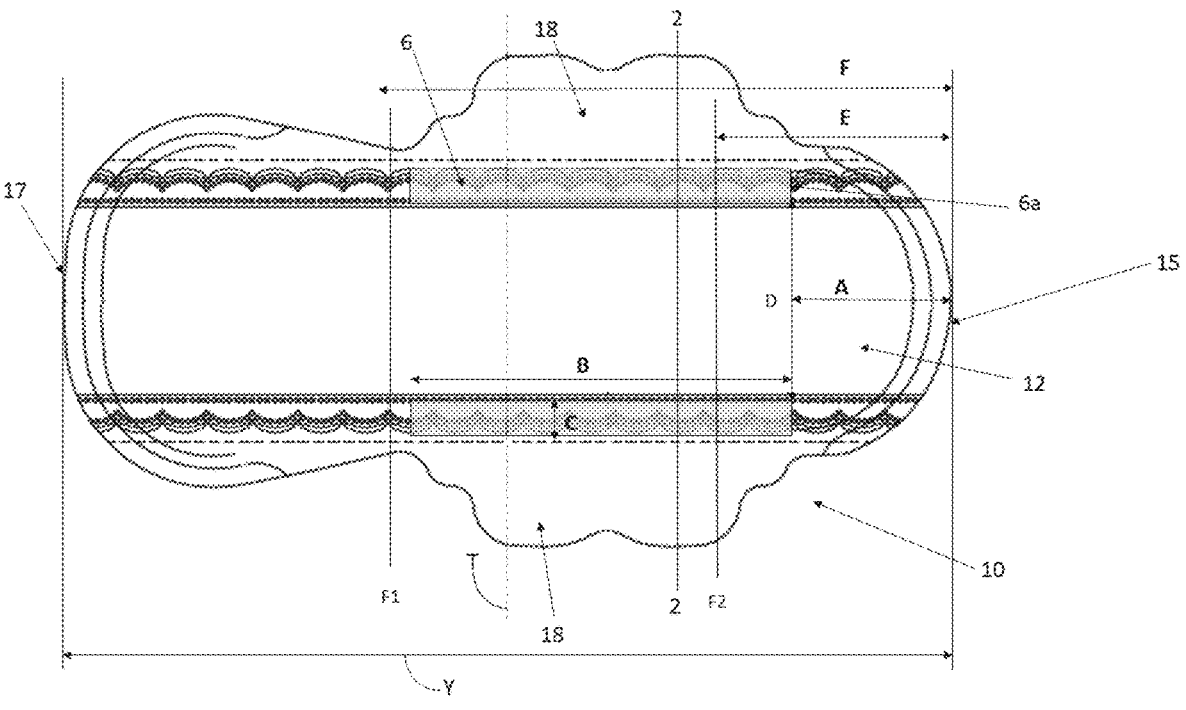
Figure 2:
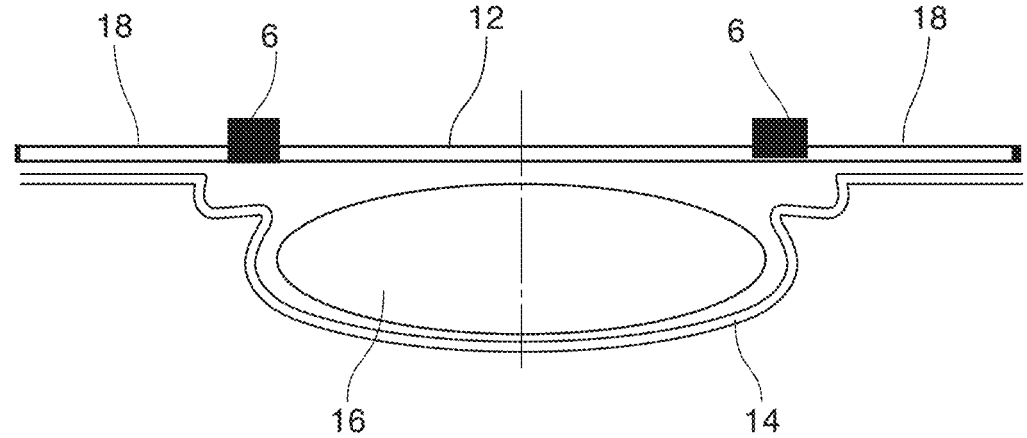
FIG. 2 is a lateral cross section taken along line 2-2 of FIGS. 1a-1b.

The absorbent article of the disclosure will now be described in detail while referencing FIG. 1-7. FIGS. 1a-1b each show a folded absorbent pad 10 having, in its flattened unfolded configuration, a longitudinal centerline (L) and a transverse centerline (T). The absorbent article 10 comprises a topsheet 12, a backsheet 14 and an absorbent core 16 disposed between topsheet 12 and backsheet 14, as shown in FIGS. 2a-2b. The article also comprises one or more folding lines (F1, F2). The folding lines can have any direction and different folding lines can have different directions. In some embodiments (such as the one depicted), the folding lines are parallel to the transversal centerline (C). The folding lines may be parallel to the longitudinal centerline (L). In some aspects, some of the folding lines may be parallel to the transverse centerline (T) and some of the folding lines may be parallel to the longitudinal centerline (L).

Preferably, the folding lines F1, F2 are parallel to the transversal centerline. F1 may be located a distance F of about 100 mm to about 235 mm, or about 165 mm to about 225 mm, or about 110 mm to about 210 mm, or about 110 mm to about 165 mm, or about 130 mm to about 210 mm, or about 150 mm to about 210 mm, or about 130 mm to about 185 mm, or about 130 mm to about 180 mm from the front end of the pad 15. F2 may be located a distance E of about 30 mm to about 115 mm, or about 40 mm to about 105 mm, or about 40 mm to about 90 mm, or about 40 mm to about 80 mm, or about 45 mm to about 95 mm, or about 55 mm to about 95 mm, or about 55 mm to about 105 mm from the front end of the pad 15. The absorbent article comprises lotion pattern areas 6, which may overlap the folding lines F1, F2.

Figure 3:
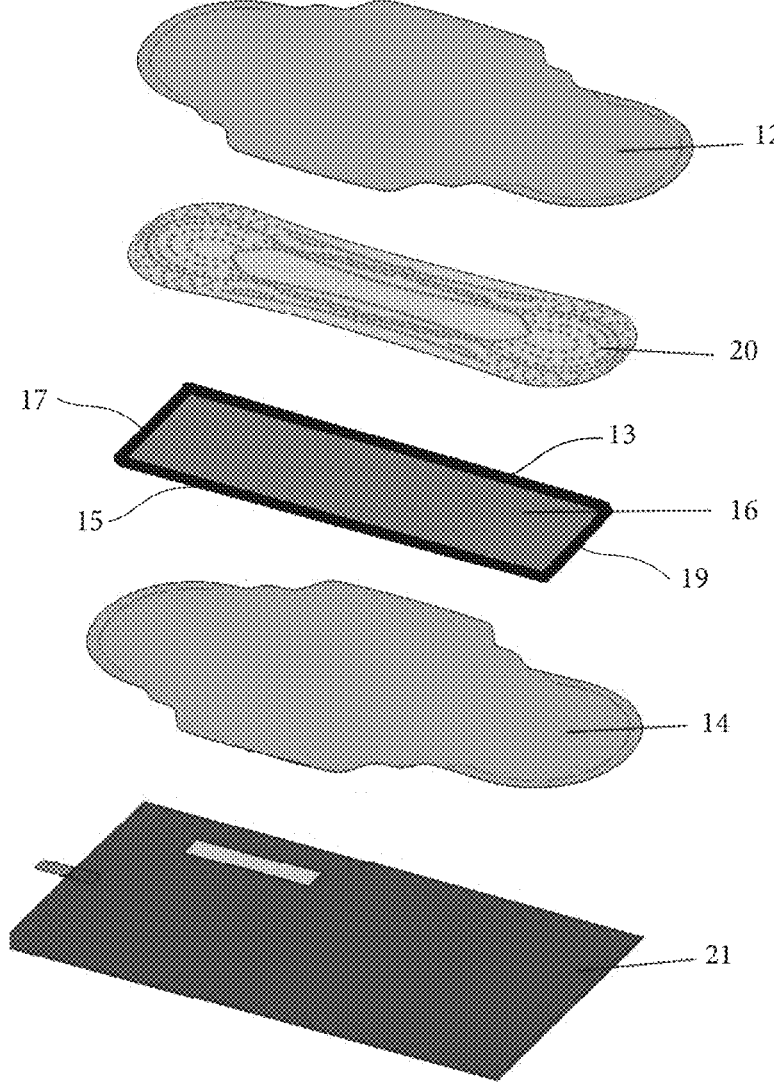
FIG. 3 is an exploded view of the layers of the absorbent article in FIGS. 1a-1b.

FIGS. 1*a*-1*b* show the body-facing surface of a folded absorbent article 10, in its flattened unfolded configuration, having a longitudinal centraline (L) and a transversal centraline (T). The pad (10) comprises: a topsheet (12), a backsheet (14) and an absorbent core (16) disposed between topsheet (12) and backsheet (14) and one or more folding lines (F1, F2). FIG. 2 shows a cross-section of the absorbent article in FIGS. 1*a*-1*b* taken along line 2-2. FIG. 3 is an exploded view showing the layers of the absorbent article in FIGS. 1*a*-1*b*.

Figure 4:
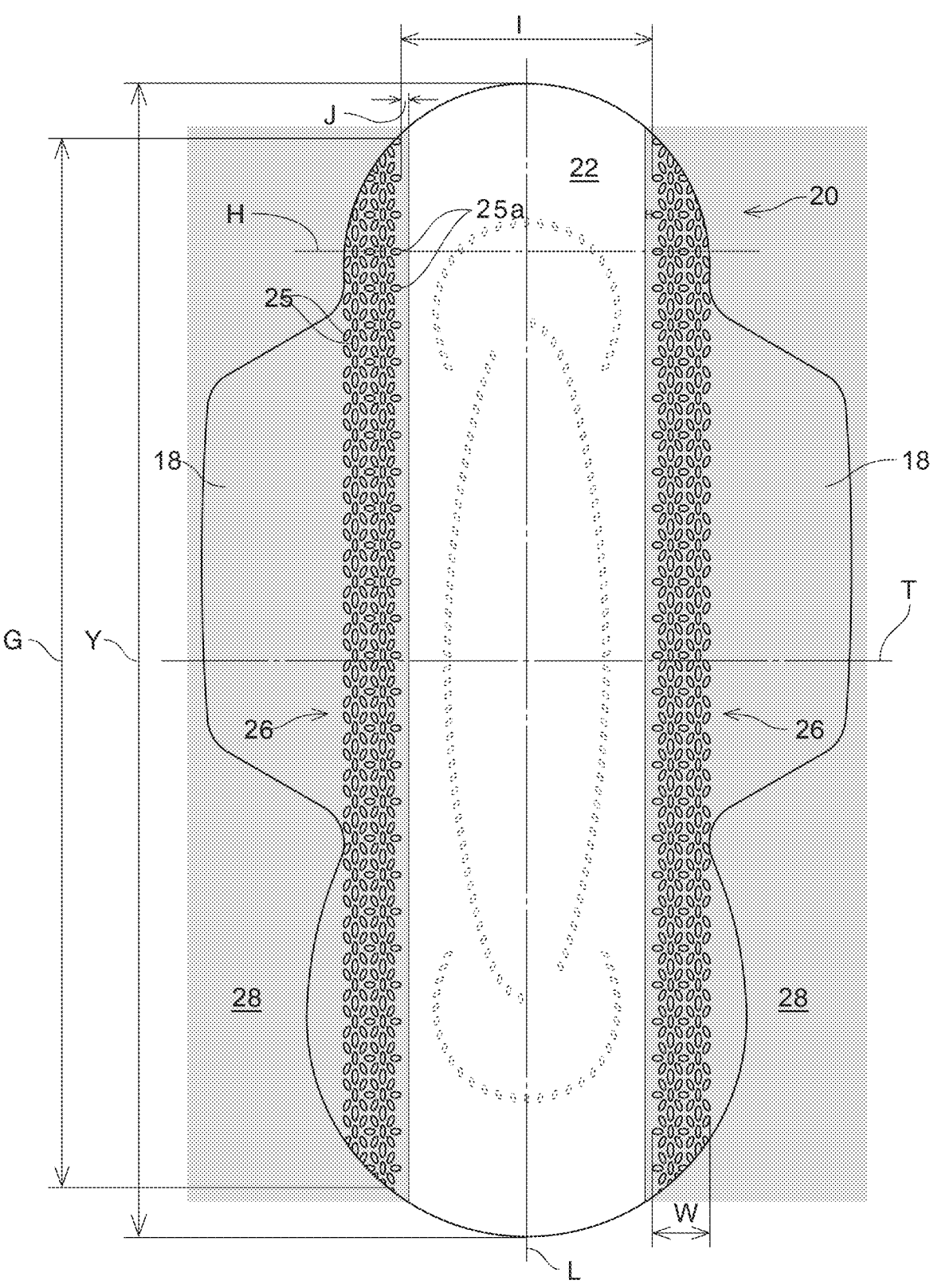
FIG. 4 is a top view of another exemplary absorbent article according to the present disclosure.
Figure 6:
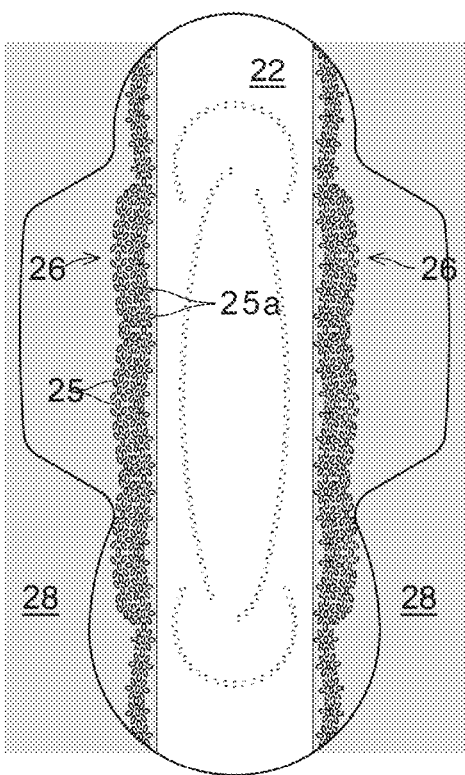
FIG. 6 is a top view of another exemplary absorbent article according to the present disclosure.
Figure 7:
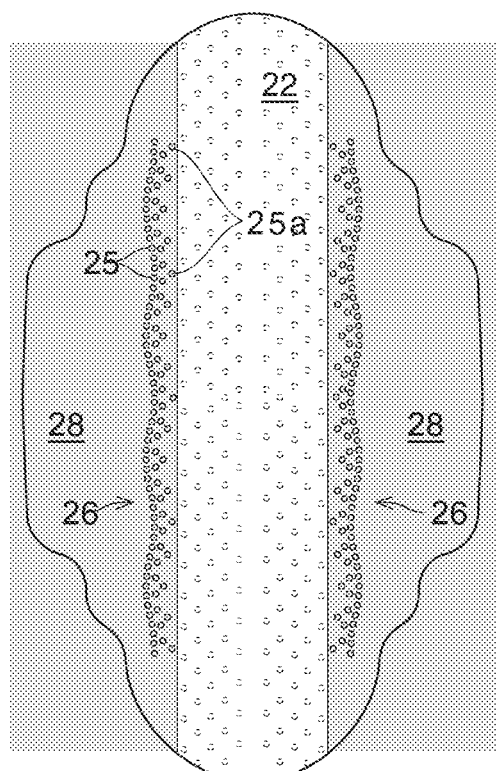
FIG. 7 is a top view of another exemplary absorbent article according to the present disclosure.

FIG. 4 shows the body-facing surface of another exemplary absorbent article 20 according to the present disclosure. The body-facing surface of the absorbent article 20 shows the topsheet 22, the lateral topsheets 28 having an embedded zone 26 comprising compressed areas 25, 25*a* on each lateral topsheet. FIG. 5(*a*) and FIG. 5(*b*) are mimetic diagrams of cross section views of exemplary absorbent articles according to the present disclosure, showing the topsheet 22, the lateral topsheets 28, the compressed areas 25, 25*a*, and the absorbent core 26 and the backsheet 24. FIGS. 6 and 7 show the body-facing surfaces of exemplary absorbent articles according to the present disclosure. It should be noted that the present invention is not limited to the configurations shown in FIGS. 1-7.

Absorbent Article

Referring to FIGS. 1*a*-1*b*, the absorbent article 10 may include a liquid permeable topsheet 12, a liquid impermeable backsheet 14, and an absorbent core 16 disposed between the topsheet 12 and the backsheet 14. The topsheet 12 and the backsheet 14 may extend beyond the outer perimeter of the absorbent core 16 and may be bonded together in laminate configuration by any suitable mechanism, including but not limited to adhesive bonding, thermal bonding, pressure bonding, etc., thereby retaining and holding the absorbent core 16 in place between the topsheet 12 and the backsheet 14. The outer surface of the backsheet forming the underside of the absorbent article 10 may have deposits of adhesive thereon. Adhesive deposits may be provided to enable the user to adhere the article to the inside of her underwear in the crotch region thereof. When article 10 is packaged, adhesive deposits may be covered by one or more sheets of release film or paper that covers/shields the adhesive deposits from contact with other surfaces until the user is ready to remove the release film or paper and place the absorbent article in her underwear. Further additional elements to improve the performance of the articles may also be used and are represented, such as a secondary topsheet 13, and/or a secondary backsheet.

Figure 5A:
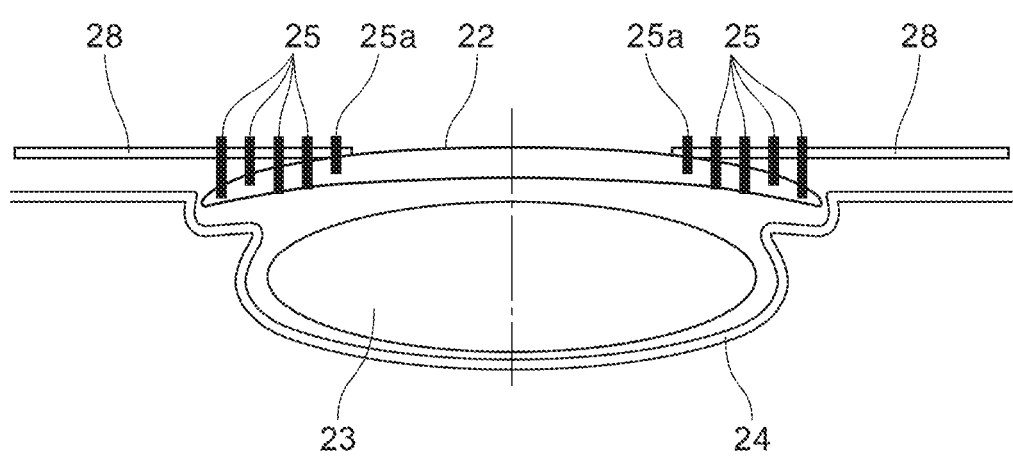
FIG. 5a is a mimetic diagram of a cross section view taken along line H of the article according to FIG. 4.
Figure 5B:
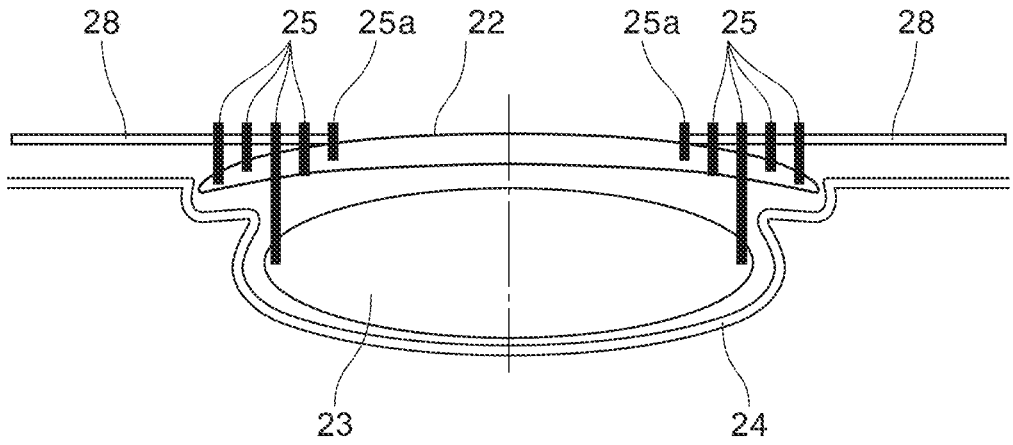
FIG. 5b is a mimetic diagram of a cross section view of modified example of embossing depth in the article shown in FIG. 4.

As shown in FIGS. 4, 5*a*, and 5*b*, in some embodiments, the absorbent articles may comprise a topsheet 22, a backsheet 24, an absorbent core 23 disposed between the topsheet 22 and backsheet 24, and a pair of lateral topsheets 28 having an embedded zone 26 on each longitudinal side of the absorbent article atop the topsheet 22. The lateral topsheets 28 may improve prevention of side leakage of fluid. The topsheet 22 and the lateral topsheets 28 partially, or completely, form the body-facing surface of the article, whilst the backsheet joined to the topsheet and/or lateral topsheets forms the garment-facing surface. The topsheet 22 covers the entire upper side of the absorbent core 23, and slightly extends laterally outward from the longitudinal sides of the absorbent core 23. It also extends outwards from the front and the back ends of the absorbent core 23, and joins with a backsheet 24 in the extensions. The lateral topsheets 28 are deposited to cover both side portions of absorbent core 23 so that the lateral topsheets cover a part of the topsheet 22 and extends outwards to join the backsheet 24 to cover sides of the absorbent article.

The lateral topsheets 28 may for example be made of all conventional type of nonwovens, such as carded thermal bonded, spun bonded, hydro entangled, melt blown, and using all range of suitable synthetic or natural fibers such as polypropylene, polyethylene, polyester, rayon, cotton, and in a mixed form or in the form of monocomponent, bicomponent fiber. For example, Pegas a.s (Czech Republic) supplies a suitable nonwoven based of bicomponent fibers made of Polypropylene (PP) as core and Polyethylene (PE) as sheath, with a polymer ratio: PP core 70%/PE sheath 30%. It may be preferred that the lateral topsheets 28 are made of a material having water-repelling properties, in other words, a hydrophobic material, to help preventing side leakage or re-wetting of the body-facing surface of the article. Examples of hydrophobic materials suitable for the lateral topsheet include hydrophobic nonwoven, and the synthetic polymeric materials cited above, in particular polyethylene, polypropylene and their mixtures.

The lateral topsheets 28 may take the form of two parallel stripes extending substantially along the whole length of the longitudinal sides of the absorbent article 20. In such case, typically, the outer side edges of the lateral topsheets are contiguous to the longitudinal sides of the article on its periphery. The inner side edges of the lateral topsheets can be linear or have any other shapes. The lateral topsheets, as shown in FIG. 4, may project outwards in the transverse direction to form side flaps or wings 18 with parts of the backsheet 24.

As shown in FIG. 4, in some embodiments, the absorbent articles comprise embedded zones 26 on each of the lateral topsheet 28 along in the longitudinal direction of the article. The embedded zone 26 is a region extending in a longitudinal direction of the absorbent article, and has a plurality of compressed areas 25, 25*a*.

As shown in FIG. 5*a*, the embedded zone 26 comprises the compressed areas 25, 25*a* where the lateral topsheet 28 and the topsheet 22 are compressed together so that at least a part of the lateral topsheet is embedded into the topsheet. In some embodiments, as shown in FIG. 2*b*, the embedded zone 26 may include compressed areas where the absorbent core 23 is also at least partially embossed together with the lateral topsheet 28 and the topsheet 22. In the compressed areas 25, 25*a*, the lateral topsheet embedded into topsheet is single layer. The embedded zones 26 having a plurality of the compressed areas where the lateral topsheets are embedded into the hydrophilic topsheet, the fluid on top of the lateral sheets can be effectively acquired inside the absorbent article as the embedded structure provides more suction of the fluid by the hydrophilic topsheet, and effectively directs the fluid to the inside the absorbent article. In addition, lateral diffusion of the fluid beyond the side edges of the absorbent core is also effectively prevented by the presence of the compressed areas and the lateral topsheets. Prevention of fluid leakage in the absorbent article may be enhanced by employing hydrophobic lateral topsheets. Alternatively, the lateral topsheet 28 and the topsheet 22 may be joined together via adhesive bonding.

The embedded zone 26 may be formed to be linear. The width W of the embedded zone 26, as shown in FIG. 4, is the longest distance in the transverse direction between two compressed areas. The width W of the embedded zone 26 may be constant along the longitudinal direction, or may not be. For example, the width W of the embedded zone 26 at one point relatively close to the transverse centerline T may be greater than the width W of the embedded zone 26 at another point relatively close to a front or back end. A width of embedded zone may be in the range of from about 2 mm to about 30 mm, preferably from about 5 mm to about 20 mm. The distance I between embedded zones 26 may be in the range of from about 30 mm to about 80 mm, preferable from about 50 mm to about 70 mm.

The embedded zone 26 in the lateral topsheet 28 has a length in the longitudinal direction having a length share of about 50% or more of relative to the length Y of the article, and cross a transverse centerline T. In some embodiments, the embedded zones 26 may extend to at least one of a front and a back end edges of the absorbent article. When the embedded zones 26 extend to a front end and back end edges of the absorbent article, it may bond the lateral topsheets 28 and the topsheet 22 without using another bonding means such as glue by providing sufficient bonding strength to the lateral topsheets 28 and the top topsheet 22.

The embedded zone 26 preferably has about 50%, more preferably 60%, of the compressed areas 25, 25a by the total area of the embedded zone 26.

In some embodiments, the compressed areas 25, 25a formed in the embedded zone 26 may be arranged substantially continuously in the longitudinal direction. In another embodiment of the present invention, the compressed areas 25, 25a formed in the embedded zone 26 may be arranged substantially continuously in the transversal direction. The term "substantially continuous(ly) in the longitudinal direction", as used herein, defines as follows: Move an imaginary straight line perpendicular to the longitudinal direction in the longitudinal direction in the plan view of the absorbent article. When the line intersects the compressed areas 25, 25a over a length of 80%, preferably 90%, more preferably 100%, of the length G of the embedded zone 26, the compressed areas are considered to be "substantially continuous(ly) in the longitudinal direction." Similarly, the term "substantially continuous(ly) in the transversal direction", as used herein, as follows: Move an imaginary straight line perpendicular to the transversal direction in the transversal direction in the plan view of the absorbent article. When the line intersects the compressed areas 25, 25a over a length of 70%, preferably 90%, more preferably 100%, of the width W of the embedded zone 26, the compressed areas are considered to be "substantially continuous(ly) in the transversal direction."

Hereinafter, "overhang" means, as shown in FIG. 4, the distance J between inner side edge of the lateral topsheet 28 and the compressed area 25a, the compressed area closest to the inner side edge. The overhang is preferably less than about 2 mm, more preferably less than about 1 mm, and more preferably substantially zero.

Outer side edge of the embedded zone 26 may extend in a transverse direction to side edge of the absorbent core 23.

Preferably, the outer side edge of the embedded zone 26 may extend outwards from the side edges of the absorbent core 23.

The embedded zones 26 may have at least one of various shapes such as circle, oval, heart shape, triangle, square, rectangle, line, and irregular shapes. The size of each compressed area may have dimension of from about 2 mm to about 10 mm, preferably from about 2 mm to about 5 mm. The distance between the dots may be narrower than about 5 mm, preferable narrow than 2 mm. The dots can be arranged regularly into straight lines or shaped lines or randomly arranged.

The embossing can be achieved with standard techniques such as thermal bond, ultrasonic bond and/or pressure. An example of a suitable process is thermal bonding wherein sheets are passed through two steel rolls where one is engraved with the visual pattern and the other is flat. In certain embodiments, one or both of the rolls are warmed to a temperature suitable to at least partially melt one or more sheet or soften one or more sheet layer, typically a temperature in the range of from about 60° C. to about 170° C.

The embossing roll may be engraved using conventional techniques such machine tooling for most embossing patterns, but it may be desirable to use acid etching or laser engraving to provide a finer engraving, and thus a finer embossed pattern. It may be desirable that the embossed pattern comprises relatively thin embossing features, much thinner than the embossed channels previously disclosed in the art, such as in WO2004/006818. Thin embossing features may provide a generally feminine and delicate look to the article. The embossing tool should therefore capable of high definition embossing, in particular with a resolution (minimum thickness of the embossed lines) of less than about 0.75 mm, in particular but not limited to between about 0.35 mm and about 0.60 mm. Similarly, the resolution of the printed pattern (corresponding to the minimum thickness of a printed line) may be of less than about 0.75 mm, in particular but not limited to between about 0.35 mm and about 0.60 mm.

Topsheet

The topsheet of the absorbent article is preferably compliant, soft feeling, and non-irritating to a wearer's skin. Further, the topsheet is liquid pervious, permitting liquids (e.g., menses and/or urine) to readily penetrate through it. A suitable topsheet may be manufactured from a wide range of materials such as woven and nonwoven materials (e.g., a nonwoven web of fibers), polymeric materials, such as apertured formed thermoplastic films, apertured plastic films, and hydroformed thermoplastic films, porous foams, reticulated foams, reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers), or a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like. The topsheet may have a basis weight of from about 10 gsm to about 100 gsm, preferably from about 30 gsm to about 80 gms to allow fast fluid penetration inside of an absorbent article.

The topsheet may be hydrophilic, semi-philic, or hydrophobic. The topsheet may be treated to be hydrophilic, hydrophobic, or semi-philic, for example, using surfactants or other means known to the person skilled in the art.

Topsheets may be formed by one or more layers made of the materials mentioned above, where one layer forms the upper surface of the absorbent article and one or more other layers are positioned immediately below it. The layer forming the upper surface of the article is typically a nonwoven layer or a formed film.

An additional layer may be optionally present between the topsheet and the absorbent core and is commonly referred to as a "secondary topsheet" or an "acquisition layer". This secondary topsheet is designed to acquire the fluid on a liquid-permeable topsheet and distribute it to the underlying absorbent core. To help ensure that the secondary topsheet transfers the fluid to the absorbent core, secondary topsheets are typically made from an air-laid-tissue web or a synthetic nonwoven that has sufficient capillarity to draw the fluid through the topsheet. To ensure that the fluid flow continues on to the absorbent core, the secondary topsheet is commonly designed with more permeability than the absorbent core and less capillarity than the absorbent core. The secondary topsheet may have a basis weight of less than 125 grams per square meter, or less than 100 grams per square meter, or less than 80 grams per square meter.

In some aspects, the absorbent articles of the present disclosure may comprise a hydrophilic nonwoven topsheet 22, which may catch body fluids and allow the fluid to readily penetrate into the absorbent core 26 of the absorbent article 20. Any conventional hydrophilic nonwoven topsheet materials may be used within the disclosure. Hydrophilic nonwoven can be made of hydrophilic fibers treated with a treatment agent, such as a hydrophilic agent, rendering the fibers hydrophilic. Alternatively, or in addition, hydrophilic nonwoven can be prepared by treating nonwoven (after nonwoven formation) with a hydrophilic agent. Such hydrophilic agents may for example include or be a surfactant. Treatment of nonwoven with surfactant can be accomplished by any of the common techniques well known to those skilled in the art. For example, the surfactant can be applied to nonwoven topsheet by spray, by padding, or by the use of transfer rolls.

Backsheet

The article of the disclosure comprises backsheet 14. The backsheet 14 may be any flexible, liquid resistant, and liquid impervious material. The backsheet prevents discharges collected by and contained in the sanitary napkin, and particularly discharges absorbed by the core, from escaping the sanitary napkin and soiling the clothing and bedding of the wearer. Preferably the backsheet is not noisy, to provide discretion for the wearer. In some executions, a secondary backsheet (discussed below) may be placed intermediate the core and the backsheet to second the backsheet, for example to provide liquid imperviousness.

The backsheet can also be vapor permeable ("breathable"), while remaining fluid impermeable. The backsheet may be manufactured from a thin plastic film, such as a microporous polyethylene or polyethylene polypropylene film, or other flexible materials, such as nonwovens. The backsheet can be formed by one or more layers and may comprise a woven or nonwoven material, polymeric films, such as thermoplastic films of polyethylene or polypropylene, or composite materials, such as a film-coated nonwoven material. A suitable material for the backsheet can be a liquid impervious thermoplastic film having a thickness of from about 0.012 mm (0.50 mil) to about 0.051 mm (2.0 mils), for example including polyethylene or polypropylene. Typically, the backsheet can have a basis weight of from about 5 g/m2 to about 35 g/m2.

The backsheet and the topsheet can be positioned respectively adjacent the garment surface and the body surface of the absorbent core. The topsheet and the backsheet are preferentially peripherally joined using known techniques, either entirely so that the entire perimeter of the sanitary article is circumscribed by such joinder or are partially peripherally joined at the perimeter. The absorbent core can be joined with the topsheet, the backsheet, or both in any manner as is known by attachment means such as those well known in the art. Embodiments of the present disclosure are envisioned where portions of the entire absorbent core are unattached to either the topsheet, the backsheet, or both. Any joined arrangement that provides for capture of the core intermediate the topsheet and the backsheet and a unitary assembly is suitable. Such an assembly has two mutually opposed major faces, one defined by the topsheet and one defined by the backsheet.

The backsheet may comprise a panty fastening means applied on its garment-facing surface for attaching the article to the undergarment of the wearer. Suitable panty fastening means include adhesive or Velcro®. When an adhesive is present, a release paper is typically also present in order to protect the adhesive before use. Pressure sensitive adhesive has been commonly found to work well for this purpose. Preferably a strip of longitudinally oriented adhesive provides good protection against either the front or the back of the article becoming detached from the wearer's undergarment. The adhesive strip may be continuous or intermittent. A particularly preferred arrangement utilizes two longitudinally oriented strips, one on each side of the longitudinal centerline. The backsheet typically extends across the whole of the absorbent structure and can extend into and form part of or all of the sideflaps, side wrapping elements or wings 18, when present.

Side flaps or wings are disclosed in the literature and are available in the marketplace. Generally, side flaps extend laterally from a central portion of the absorbent article and are intended to be folded around the edges of the wearer's panties in the crotch region. Thus, the flaps are disposed between the edges of the wearer's panties in the crotch region and the wearer's thighs. Commonly, the flaps are provided with an attachment means for affixing the flaps to the underside of the wearer's panties. In most cases the attachment means that is similar to or identical to the panty fastening means of the backsheet, e.g., a layer of adhesive. The flaps may serve at least two purposes: the flaps may prevent exudates from soiling the edges of the wearer's panties, and the flaps may help stabilize the napkin from shifting out of place, especially when the flaps are affixed to the underside of the panties.

As noted above, side flaps can be formed as an extension of an elements forming the absorbent article, such as the backsheet, the topsheet, the absorbent core, the secondary topsheet (if present), or a combination thereof. Side flaps may also be separate elements that are attached to the sides of the absorbent article along its perimeter.

Absorbent Core

The article of the disclosure comprises an absorbent core 16 disposed between the topsheet 12 and the backsheet 14. As used herein, the term "absorbent core" refers to a material or combination of materials suitable for absorbing, distributing, and storing aqueous fluids such as urine, blood, menses, and other body exudates.

The size and shape of the absorbent core can be altered to meet absorbent capacity requirements, and to provide comfort to the wearer. As with the other elements of the articles of the disclosure, there are no particular requirements for the absorbent core and any standard liquid-absorbent material known in the art for use in absorbent articles will normally be suitable.

Non-limiting examples of liquid-absorbent materials suitable for use as the absorbent core include comminuted wood pulp which is generally referred to as airfelt; creped cellulose wadding; absorbent gelling materials including superabsorbent polymers such as hydrogel-forming polymeric gelling agents; chemically stiffened, modified, or crosslinked cellulose fibers; meltblown polymers including coform; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof. The core, as the article itself, may be generally planar, i.e. does not have a significant variation in thickness.

Typically the absorbent core is rectangularly shaped, for ease of manufacturing. However, the core may be differently shaped, for example there is frequently a wearer preference for an absorbent core which is narrower at the center than at the ends, to comfortably accommodate the legs, and obviate or minimize occurrences of bunching or wadding of the core. Oval shaped core have also been proposed (see, e.g., WO2005/084596). Further generic and specific information regarding absorbent cores can be found for example in WO0207662A1 and WO09119471, which are hereby incorporated by reference herein.

Lotion Composition

The lotion composition may be a hydrophobic lotion or a hydrophilic lotion. Preferably, the lotion composition is a hydrophobic lotion comprising hydrophobic skin-friendly ingredients, as in a skin cream. Without being bound by theory, it is believed that superior benefits may be provided by the combination of a hydrophobic topsheet and a hydrophobic lotion. A lotion composition is considered hydrophobic, for example, if the hydrophilic/lipophilic balance (HLB) is less than or equal to 7.

The lotion composition is partially transferred to the skin of the wearer during usage of the absorbent article, where it provides barrier properties to help reduce the adherence of menses, to reduce abrasion between the skin and the absorbent article, e.g., the wings of the article, and to reduce potential skin irritation.

The lotion compositions may comprise a select combination of skin treatment agents such as hexamidine, zinc oxide, and niacinamide which are highly effective in the prevention and treatment of erythema, malodor, and bacterial skin disorders, especially when these lotion compositions are administered to the skin from application on absorbent articles. The term "skin treatment agent" as used herein refers to materials that when applied topically and internally to the skin are capable of preventing, reducing, and/or eliminating any occurrence of skin disorders, particularly skin disorders associated with erythema, malodor, and bacterial infections. The term "skin disorders" as used herein refers to symptoms associated with irritating, acute, or chronic skin abnormalities. Examples of such symptoms include, but are not limited to, itching, inflammation, rash, burning, stinging, redness, swelling, sensitivity, sensation of heat, flaking/scaling, malodor, and the like.

The lotion compositions may comprise hexamidine at concentrations ranging from about 0.001% to about 0.1%, from about 0.005% to about 0.1%, or even from about 0.01% to about 0.1% by weight of the composition.

Examples of hexamidine are disclosed in US Pat. Pub. No. 2003/0206943, which is hereby incorporated by reference herein.

The lotion compositions may comprise zinc oxide skin treatment agent at concentrations ranging from about 0.001% to about 10%, preferably from about 0.005% to about 5%, more preferably from about 0.005% to about 2%, most preferably from about 0.01% to about 1% by weight of the composition. Examples of zinc oxide are disclosed in US Pat. Pub. No. 2003/0206943, which is hereby incorporated by reference herein. The zinc oxide skin treatment agent can be included in the compositions as an individual zinc oxide compound or a combination of zinc oxides, provided that the individual or combined zinc oxide can readily combine with the hexamidine and niacinamide skin treatment agents to provide antimicrobial benefits.

The lotion compositions may comprise niacinamide skin treatment agent as an individual niacinamide or as a combination of niacinamides at a total niacinamide concentration ranging from about 0.01% to about 10%, preferably from about 0.05% to about 5%, more preferably from about 0.2% to about 2% by weight of the lotion composition. Examples of niacinamide are disclosed in US Pat. Pub. No. 2003/0206943, which is hereby incorporated by reference herein. The niacinamide skin treatment agent provides for skin conditioning benefits as well as providing for increased efficacy of the skin treatment agents in controlling skin disorders.

The lotion compositions may comprise from about 0.001% to about 10%, preferably from about 0.005% to about 5%, more preferably from about 0.05% to about 1% by weight of the lotion composition of panthenol. Panthenol provides for skin emolliency benefits that can leave the skin feeling smooth, soothing, and soft during and after interaction of the skin tissues with the skin treatment agents. The lotion compositions of the present disclosure can include an individual panthenol compound or a mixture of panthenol compounds. Examples of panthenol are disclosed in US Pat. Pub. No. 2003/0206943, which is hereby incorporated by reference herein.

The lotion compositions may comprise from about 0.01% to about 10%, preferably from about 0.02% to about 5%, more preferably from about 0.05% to about 2% by weight of the lotion composition of glycerine. Glycerine also provides for skin emolliency benefits such as smooth, soothing, and soft feeling skin, as well as being a dispersing agent for the niacinamide skin treatment agent.

The lotion compositions may comprise from about 0.0001% to about 10%, preferably from about 0.001% to about 5%, more preferably from about 0.005% to about 2% by weight of the lotion composition of chamomile oil. Chamomile oil also provides for skin benefits such as soothing. Chamomile oil is commonly prepared as an oil extract of chamomile flowers. An example of a commercially available chamomile oil include Phytoconcentrol Chamomile which is available from Dragoco Incorporation (Totowa, N.J.).

The lotion compositions may comprise a carrier for the skin treatment agents. The carrier can be included in the compositions as an individual carrier or a combination of carrier ingredients, provided that the total carrier concentration is sufficient to provide transfer and/or migration of the skin treatment agents onto the skin. The carrier can be a liquid, solid, or semisolid carrier material, or a combination of these materials, provided that the resultant carrier forms a homogenous mixture or solution at selected processing temperatures for the resultant carrier system and at processing temperatures for combining the carrier with the skin treatment agents in formulating the lotion compositions herein. Processing temperatures for the carrier system typically range from about 60° C. to about 90° C., more typically from about 70° C. to about 85° C., even more typically from about 70° C. to about 80° C.

The lotion compositions typically comprise the carrier at a total carrier concentration ranging from about 60% to about 99.9%, preferably from about 70% to about 98%, more preferably from about 80% to about 97% by weight of the lotion composition. Suitable carrier compounds include petroleum-based hydrocarbons having from about 4 to about 32 carbon atoms, fatty alcohols having from about 12 to about 24 carbon atoms, polysiloxane compounds, fatty acid esters, alkyl ethoxylates, lower alcohols having from about 1 to about 6 carbon atoms, low molecular weight glycols and polyols, fatty alcohol ethers having from about 12 to about 28 carbon atoms in their fatty chain, lanolin and its derivatives, glyceride and its derivatives including acetoglycerides and ethoxylated glycerides of C12-C28 fatty acids, and mixtures thereof. Alternatively or in combination with, the carrier may also be composed of polysiloxane compounds non-limiting examples include dimethicones (1-100,000,000 centistoke), cyclomethicones, alkylated silicones (hair conditioning agents), silicone gums, silicone gels, silicone waxes, copolymers of silicone (vinyl dimethicone polymers, phenyl vinyl dimethicone polymers, alkylated silicone polymers, polyethylene oxide/silicone copolymers, polyethylene oxide/alkyl silicone copolymers), and mixtures thereof.

Nonlimiting examples of suitable petroleum-based hydrocarbons having from about 4 to about 32 carbon atoms include mineral oil, petrolatum, isoparaffins, various other branched chained hydrocarbons, and combinations thereof. Mineral oil is also known as "liquid petrolatum", and usually refers to less viscous mixtures of hydrocarbons having from about 16 to about 20 carbon atoms. Petrolatum is also known as "mineral wax", "petroleum jelly", and "mineral jelly", and usually refers to more viscous mixtures of hydrocarbons having from about 16 to about 32 carbon atoms. An example of commercially available petrolatum include petrolatum sold as Protopet® 15 which is available from the Witco Corporation located in Greenwich, Conn.

Nonlimiting examples of suitable fatty alcohols having from about 12 to about 24 carbon atoms include saturated, unsubstituted, monohydric alcohols or combinations thereof, which have a melting point less than about 110° C., preferably from about 45° C. to about 110° C. Specific examples of fatty alcohol carriers for use in the lotion compositions of the present disclosure include, but are not limited to, cetyl alcohol, stearyl alcohol, cetearyl alcohol, behenyl alcohol, arachidyl alcohol, lignocaryl alcohol, and combinations thereof. Examples of commercially available cetearyl alcohol is Stenol 1822 and behenyl alcohol is Lanette 22, both of which are available from the Cognis Corporation located in Cincinnati, Ohio.

Nonlimiting examples of suitable fatty acid esters include those fatty acid esters derived from a mixture of C12-C28 fatty acids and short chain (C1-C8, preferably C1-C3) monohydric alcohols preferably from a mixture of C16-C24 saturated fatty acids and short chain (C1-C8, preferably C1-C3) monohydric alcohols. Representative examples of such esters include methyl palmitate, methyl stearate, isopropyl laurate, isopropyl myristate, isopropyl palmitate, ethylhexyl palmitate, and mixtures thereof. Suitable fatty acid esters can also be derived from esters of longer chain fatty alcohols (C12-C28, preferably C12-C16) and shorter chain fatty acids such as lactic acid, specific examples of which include lauryl lactate and cetyl lactate.

Nonlimiting examples of suitable alkyl ethoxylates include C12-C22 fatty alcohol ethoxylates having an average degree of ethoxylation of from about 2 to about 30. Nonlimiting examples of suitable lower alcohols having from about 1 to about 6 carbon atoms include ethanol, isopropanol, butanediol, 1,2,4-butanetriol, 1,2 hexanediol, ether propanol, and mixtures thereof. Nonlimiting examples of suitable low molecular weight glycols and polyols include ethylene glycol, polyethylene glycol (e.g., Molecular Weight 200-600 g/mole), butylene glycol, propylene glycol, polypropylene glycol (e.g., Molecular Weight 425-2025 g/mole), and mixtures thereof.

In some embodiments, the carrier comprises a combination of one or more petroleum-based hydrocarbons and one or more fatty alcohols described hereinabove. When one or more petroleum-based hydrocarbons having from about 4 to about 32 carbon atoms are used in combination with one or more fatty alcohols having from about 12 to about 22 carbon atoms, the petroleum-based hydrocarbons are included at total concentrations ranging from about 20% to about 99%, preferably from about 30% to about 85%, more preferably from about 40% to about 80% by weight of the lotion composition; wherein the fatty alcohols are included at total concentrations ranging from about 0.2% to about 65%, preferably from about 1% to about 50%, more preferably from about 2% to about 40% by weight of the lotion composition.

It is believed that a petroleum-based carrier system comprising C4-C32 hydrocarbons, C12-C22 fatty alcohols, and finned silica provides a homogeneous mixture of the carrier, skin treatment agents, and any optional ingredients wherein this homogeneous mixture ensures sufficient contact between the skin and skin treatment agents to result in effective prevention and treatment of skin disorders. The fumed silica suitable for inclusion in the preferred petroleum-based carrier system, or with any other carrier described herein, includes colloidal pyrogenic silica pigments which are sold under the Cab-O-Sil® tradename, and which are commercially available from the Cabot Corporation located in Tuscola, Ill. These colloidal pyrogenic silica pigments are submicroscopic particulated pyrogenic silica pigments having mean particle sizes ranging from about 0.1 microns to about 100 microns. Specific examples of commercially available Cab-O-Sil® silica pigments include Cab-O-Sil® TS-720 (a polydimethylsiloxane treated fumed silica), Cab-O-Sil® TS-530 (a trimethyl silanized fumed silica), and Cab-O-Sil® TS-610 (a dimethyldisilanized fumed silica). The fumed silica provides the lotion compositions with desired viscosity or thickening properties, and is typically included at concentrations ranging from about 0.01% to about 15%, preferably from about 0.1% to about 10%, more preferably from about 1% to about 5% by weight of the lotion composition.

The fumed silica can be used alone or in combination with other optional viscosity or thickening agents such as talc, bentonites including treated bentonites, hectorites including treated hectorites, calcium silicates including treated calcium silicates, magnesium silicates, magnesium aluminum silicates, zinc stearates, sorbitol, colloidal silicone dioxides, spermaceti, camuba wax, beeswax, candelilla wax, paraffin wax, microcrystalline wax, castrol wax, ceresin, esparto, ouricuri, rezowax, polyethylene wax, C12-C24 fatty acids, polyhydroxy fatty acid esters, polyhydroxy fatty acid amides, polymethacrylate polymers, polymethacrylate and styrene copolymers, and combinations thereof. These other optional viscosity modifying or thickening agents are also included at total concentrations ranging from about 0.01% to about 15% by weight of the lotion composition. A nonlimiting specific example of another suitable viscosity or thickening agent include bentonite sold as Benton® 38 which is available from the Rheox Incorporation.

It is preferable that the carrier be hydrophobic. Further, it is preferable that the lotion composition of the present disclosure comprise no surfactant. Therefore, in preferred embodiments, the lotion has a level of hydrophobicity at least as great as that of the topsheet, and the hydrophobicity of the lotion is primarily due to the lack of a surfactant component. If, under some conditions, there is a need to raise the wettability of the hydrophobic carrier, one may optionally add a wetting agent such as polyoxyethylene alkyl ethers, alkyl ethoxylates, alkylethoxylated amines, polyethylene glycol esters, and/or sorbitan fatty acid esters generally having a low degree of ethoxylation and HLB values below about 7. Suitable additives will be miscible with the carrier so as to form a homogenous mixture. Typically, these wetting agents are nonionic to be mild for the skin, but also to avoid other undesirable effects on any underlying tissue laminate structure, e.g., reductions in tensile strength. Suitable wetting agents will typically have HLB values below 10, preferably below 9, more preferably below 8, and even more preferably below 7.

Lotion Pattern

Lotion is applied to the topsheets of the absorbent articles according to a pre-determined lotion application pattern, which is more simply referred herein as the lotion pattern. The lotion pattern covers certain areas of the topsheet, referred to herein as the lotion pattern areas. While not wishing to be bound by theory, it is believed that the dimensions and placement of the lotion pattern areas may be optimally selected to allow for efficient coverage and transfer of the lotion to the wearer's skin, without interfering with the packaging material, the adhesive disposed on the wings, and/or fluid absorption through the topsheet. The lotion is typically hydrophobic and thus may hinder fluid absorption if, for example, the total area covered by the lotion pattern areas is too large. The total area covered by the lotion pattern areas may be from about 1% to about 15%, or from about 1% to about 10%, or from about 1% to about 8% of the footprint of the topsheet. Having a coverage lower than 1% may be insufficient to provide an efficient lotion deposition over a sufficiently large area of the wearer's skin, while having a lotion pattern area higher than 15% may hinder the overall fluid acquisition.

More specifically, in the context of tri-folded absorbent pad, the lotion is preferably confined within the central portion or within the central and front portions of the pad. In particular, it is preferred that the rear portion of the pad is substantially free of lotion. During manufacturing, the rear portion of the pad is generally folded over the central portion of the pad. It is believed that the application of lotion on the rear portion of the pad may, upon folding of the rear portion over the central portion, interfere with the adhesive disposed on the garment-facing sides of the wings, which are generally folded over the central portion and under the rear portion, or result in smearing on the packaging material/wrapper or leakage of the lotion. Additionally, lotion applied on the rear portion of the pad may, upon folding of the rear portion over the central portion—particularly if tracking errors occur in the folding process, transfer to the topsheet in the central region of the pad and interfere with fluid absorption through the topsheet. Accordingly, lotion pattern areas 6 may have a length B of from about 90 mm to about 150 mm, preferably from 100 mm to about 140 mm, more preferably about 130 mm. Furthermore, the front ends 6a of the lotion pattern areas 6 may be from about 30 mm to about 70 mm, or from about 40 mm to about 60 mm, or from about 40 mm to about 55 mm, or from about 55 mm to about 70 mm, or from about 60 mm to about 70 mm, from the front end 15 of the pad.

The lotion is furthermore advantageously applied along the inner side edges 9 of the wings or side flaps 18, as shown in FIGS. 1a-1b, with the wings themselves being substantially free of lotion. In other words, the lotion may cover from about 0% to about 3%, or from about 0.01% to about 3%, or from about 0.1% to about 3% of the footprint of each wing. In particular, in embodiments of the absorbent articles that comprise embedded zones 26, as shown in FIG. 4, the lotion preferably covers less than 3% (e.g., from about 0.01% to about 3%) of the footprint of each wing, because the overhang J (defined above and shown in FIG. 4) is preferably less than about 2 mm. If the overhang J were greater than 2 mm, then lotion (even where the lotion covers less than 3% of the footprint of each wing) may transfer to and interfere with the blade used to cut out the final shape of the pad.

It is believed that application of the lotion along the inner side edges of the wings significantly reduces skin irritation, because the lotion reduces friction between the user's inner thighs and wings. Application of lotion on the wings, e.g., beyond the inner side edges of the wing and/or on greater than 3% of each wing footprint, is not believed to address skin irritation, because it is the inner side edges of the wings that contact the user's inner thighs. The width of the stripes C may accordingly range from 5 mm to 20 mm for at least some of the stripes and advantageously for all the stripes, in particular from 5 mm to 15 mm, or from 5 mm to 10 mm.

The lotion is also preferably applied outside of the footprint of the absorbent core. In other words, the lotion applied on the topsheet preferably does not extend beyond the transversal side edges 17, 19 and longitudinal side edges 13, 15 of the absorbent core 16 (as shown in FIG. 3) to overlap the absorbent core 16. Because the lotion is typically hydrophobic, it is desirable to keep the portion of the topsheet that overlaps the absorbent core free of lotion. The footprint of the absorbent core is the area formed by the transversal side edges 17, 19 and longitudinal side edges 13, 15 of the absorbent core. The footprint and its area can be directly read from the manufacturer specification of the absorbent core or, if the specification is not directly available, the core footprint's area can be measured directly on the absorbent core 16. The lotion pattern area can be similarly directly read from the manufacturer's specification, or if these are not available can be measured directly on the topsheet of the article. Lotion pattern are usually easily recognizable on the topsheet due the visual contrast between the topsheet's lotion-covered areas and the lotion-free areas. Lotions can also be slightly sticky due to some of their ingredients so that a fine powder like talc may be used to highlight the lotion pattern of an unknown product. The lotion pattern area can thus be measured experimentally using a ruler or by taking a digital picture which is then treated using any standard picture analysis software.

The lotion pattern areas 6 may have at least one of various shapes such as circle, oval, heart shape, triangle, square, rectangle, line, and irregular shapes. The lotion pattern is advantageously applied as a plurality of longitudinally-oriented stripes (also called slots), which are separated from one another in the transversal direction. By longitudinally-oriented it is meant parallel to the longitudinal direction.

Such a lotion pattern can be applied on the topsheet using a lotion applicator placed on the manufacturing line and having a series of lotion outlets, as is known in the art. The lotion applicator can be switched on and off extremely rapidly to obtain the desired length and placement of the stripes on the topsheet of the individual articles. The width of the stripes is defined by the width of the outlets. The stripes may all have the same width or the stripes may have different widths. The stripes may typically have all the same length in the longitudinal direction, but it is not excluded that the stripes may have different lengths. The lotion pattern is typically symmetrically disposed relative to the longitudinal centerline.

The lotion pattern of the disclosure advantageously comprises at least 2 and up to 10 longitudinally-oriented stripes. Each of these stripes is separated from one another in the transversal direction. The lotion pattern may in particular comprise from 2 to 9 stripes of lotion, more particularly from 2 to 8 stripes, that is 2, 3, 4, 5, 6, 7, 8 or 9 stripes. Preferably, the lotion pattern comprises 2 stripes, where each stripe corresponds to one of the user's thighs. The distance D between the two stripes or lotion pattern areas 6 may be from about 50 mm to about 90 mm, preferably from about 50 mm to about 80 mm, more preferably 60 mm. Each stripe may be continuous, as represented in the FIGS. 1*a*-1*b*, but it is not excluded that one or more stripes may be discontinuous. The basis weight at which the lotion is applied is typically the same for each stripe. Typical basis weight for the lotion deposited on the topsheet may for example range from 5 gsm to 20 gsm, in particular 10 gsm to 12 gsm.

While not wishing to be bound by theory, it is believed that it is advantageous to have at least two lotion stripes, so that at least one lotion stripe is on each side of the longitudinal centerline for a more consistent lotion deposition on each thigh of the wearer. The lotion stripe on each side of the longitudinal centerline may comprise multiple narrower stripes.

Secondary Topsheet

The article of the disclosure may optionally comprise a secondary topsheet layer 20 intermediate the topsheet 12 and the absorbent core 16.

Such a secondary topsheet 20 may be manufactured from a wide range of materials such as woven, nonwoven materials, polymeric materials such as apertured formed thermoplastic films, apertured plastic film, hydro formed thermoplastic films, porous foams, reticulated foams, reticulated thermoplastic films and thermoplastic scrims. Any material described hereinbefore for the topsheet can be used for the secondary topsheet. The secondary topsheet 20 may underly the topsheet on the entire surface thereof, i.e., the secondary topsheet extends to the periphery of the topsheet, so that the secondary topsheet underlies the topsheet on the entire inner surface of the topsheet.

The purpose of the secondary topsheet is normally to readily transfer the acquired body fluid from the topsheet to the absorbent core, the transfer of fluid occurring not only vertically in the thickness of the secondary topsheet, but also along the length and the width directions of the absorbent product. This helps the fluid capacity of the underlying storage layer to be fully utilized. Although preferred, the presence of secondary topsheet is however optional.

Secondary Backsheet

The article of the disclosure may comprise a secondary backsheet intermediate the absorbent core 16 and the backsheet 14. The use of a secondary backsheet is particularly indicated in presence of air permeable backsheet. The purpose of the secondary backsheet is to retard or prevent liquid from passing from the absorbent core to the outside of the product, while allowing free air flow through it. A particularly suitable example of secondary backsheet is a resilient three dimensional polymeric web, which consist of a liquid impervious film which has apertures forming capillarity or cones. The film with capillaries or cones is oriented such that the apex of the cones faces the absorbent core, thereby inhibiting or preventing the passage of fluid. The capillaries or cones can have a slanted shape, in order to partly close or completely close when compressed.

Release Paper

The outward-facing surface of the backsheet 14, which is coated with adhesive, may be provided with a protective cover that is removed prior to use. The protective cover may be a silicone coated release paper, a plastic film or any other easily removable cover. The protective cover may be in a single piece or in a multitude of pieces, e.g. to cover the individual adhesive areas. It also can perform other functions such as providing individualized packaging for the article or provide a disposal function. Any commercially available release paper or film may be used. Suitable examples include BL 30 MG-A SILOX EI/O, BL 30 MG-A SILOX 4 P/O available from Akrosil Corporation, and M&W films available from Gronau in Germany, under the code X-5432.

Method of Manufacture

The absorbent articles of the present disclosure may comprise the usual layers or components normally found in commercially available standard articles, and the layers may be joined together by standard means, such as embossing (e.g. thermal bonding), gluing, or a combination thereof. The articles may be produced industrially by conventional means.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A folded absorbent pad having, in its flattened unfolded configuration, a longitudinal centerline and a transverse centerline, the pad comprising:

a topsheet, a backsheet, an absorbent core disposed between the topsheet and the backsheet, wherein the topsheet and the backsheet are joined to form wings on the longitudinal sides of the pad;

one or more folding lines that define a front portion, a central portion, and a rear portion of the pad; and a lotion pattern disposed on the body-facing surface of the topsheet, the lotion pattern comprising at least two lotion pattern areas disposed adjacent to and extending along the inner side edges of the wings, parallel to the longitudinal centerline, wherein each of the at least two lotion pattern areas have a width of less than about 20 mm, wherein a portion of the topsheet that overlaps the absorbent core is substantially free of lotion pattern areas, wherein the wings are substantially free of lotion pattern areas, and wherein the rear portion of the pad is substantially free of lotion pattern areas.

2. The absorbent pad according to claim 1, wherein the lotion pattern areas are each about 90 mm to about 150 mm in length.

3. The absorbent pad according to claim 1, wherein the lotion pattern areas are each about 5 mm to about 15 mm in width.

4. The absorbent pad according to claim 1, wherein the front ends of the lotion pattern areas are a distance A of about 30 mm to about 70 mm from a front end of the absorbent pad.

5. The absorbent pad according to claim 1, wherein the distance D between the lotion pattern areas is about 50 mm to about 90 mm.

6. The absorbent pad according to claim 1, wherein the absorbent pad comprises a first folding and a second folding line.

7. The absorbent pad according to claim 6, wherein the first folding line is a distance F of about 110 mm to about 225 mm from the front end of the pad and the second folding line is a distance E of about 40 mm to about 105 mm from the front end of the pad.

8. The absorbent pad according to claim 1, wherein the topsheet is a hydrophobic nonwoven sheet.

9. The absorbent pad according to claim 1, wherein the topsheet is a hydrophilic nonwoven sheet.

10. The absorbent pad according to claim 1, wherein the topsheet is a semi-hydrophilic nonwoven sheet.

11. The absorbent pad according to claim 1, wherein each of the lotion pattern areas comprises a basis weight of about 5 gsm to 20 gsm.

* * * * *